United States Patent
Ford et al.

(10) Patent No.: US 11,929,152 B1
(45) Date of Patent: Mar. 12, 2024

(54) SYSTEMS, METHODS, AND APPARATUSES TO PREDICT PAIRS OF ENZYME PRIMARY SEQUENCES AND SUBSTRATES AND AN INTERACTION PROBABILITY FOR EACH PREDICTED PAIR

(71) Applicant: Amazon Technologies, Inc., Seattle, WA (US)

(72) Inventors: Alexander Sewall Ford, Seattle, WA (US); Zachary Wu, College Station, TX (US); Layne Christopher Price, Seattle, WA (US); Franziska Seeger, Seattle, WA (US); Yen Ling Adelene Sim, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 898 days.

(21) Appl. No.: 16/896,877

(22) Filed: Jun. 9, 2020

(51) Int. Cl.
  *G01N 33/48* (2006.01)
  *G06N 3/044* (2023.01)
  *G16B 5/20* (2019.01)
  *G16B 15/00* (2019.01)
  *G16B 40/00* (2019.01)

(52) U.S. Cl.
  CPC ............ *G16B 40/00* (2019.02); *G06N 3/044* (2023.01); *G16B 5/20* (2019.02); *G16B 15/00* (2019.02)

(58) Field of Classification Search
  None
  See application file for complete search history.

(56) References Cited

PUBLICATIONS

Chen, Lifan, et al. "TransformerCPI: improving compound-protein interaction prediction by sequence-based deep learning with self-attention mechanism and label reversal experiments." Bioinformatics 36.16 (2020): 4406-4414.*
Karimi, Mostafa, et al. "DeepAffinity: interpretable deep learning of compound-protein affinity through unified recurrent and convolutional neural networks." Bioinformatics 35.18 (2019): 3329-3338.*
Karimi, Mostafa, et al. "DeepAffinity: interpretable deep learning of compound-protein affinity through unified recurrent and convolutional neural networks." Supplemental Bioinformatics 35.18 (2019): 3329-3338.*
Li, Shuya, et al. "MONN: a multi-objective neural network for predicting compound-protein interactions and affinities." Cell Systems 10.4 (2020): 308-322.*
Vaswani, Ashish, et al. "Attention is all you need." Advances in neural information processing systems 30 (2017).*
Shankar, Shiv, and Sunita Sarawagi. "Posterior attention models for sequence to sequence learning." International Conference on Learning Representations. 2018.*
Serrano.Academy,"AfriendlyintroductiontoRecurrentNeuralNetworks," uploadedAug. 18, 2017 RetrievedfromInternet:<https://Awww.youtube.com/watch?v=UNmqTiOnRfg>.*
AlQuraishi. Cell Systems 8: 292-301.2019. (Year: 2019).
Ho. Nature Methods 17: 79-85. 2020. (Year: 2020).
Mrozek. Journal of Grid Computing 13: 561-585. 2015. (Year: 2015).
Non-Final Office Action, U.S. Appl. No. 16/896,907, dated Mar. 9, 2023, 25 pages.
Sucholutsky. PeerJ Computer Science 5: e210. 2019. (Year: 2019).
AlQuraishi, Mohammed, End-to-End Differentiable Learning of Protein Structure, Cell Systems, Apr. 24, 2019, pp. 292-301 (14 pages), vol. 8.
Anand, Namrata and Huang, Po-Ssu, Generative Modeling for Protein Structures, 32nd Conference on Neural Information Processing Systems (NeurIPS 2018), Montreal, Canada, 12 pgs.
Anand, Namrata et al., Fully Differentiable Full-Atom Protein Back-Bone Generation, Published as a workshop paper at International Conference on Learning Representations (ICLR) (2019), 10 pgs.
Arnold, Frances H., Design by Directed Evolution, Acc. Chem. Res. (1998), pp. 125-131, vol. 31/ No. 31.
Bileschi, Maxwell L. et al., Using Deep Learning to Annotate the Protein Universe, bioRxiv preprint; 2019, 21 pgs., https://doi.org/10.1101/626507.
Brandenberg, Oliver F. et al., Exploiting and Engineering Hemoproteins for Abiological Carbene and Nitrene Transfer Reactions, Curr Opin Biotechnol.; Oct. 2017, pp. 102-111, vol. 47.
Butler, Keith T. et al., Machine learning for molecular and materials science, Nature; Jul. 2018, pp. 547-555, vol. 559, https://doi.org/10.1038/s41586-018-0337-2.
Chen, Hongming et al., The rise of deep learning in drug discovery, Drug Discovery Today; Jun. 2018, pp. 1241-1250, vol. 23 / No. 6.
Cornish-Bowden, Athel, Current IUBMB recommendations on enzyme nomenclature and kinetics, Perspectives in Science; 2014, pp. 74-87.
Costello, Zak; Martin Garcia, Hector, How to Hallucinate Functional Proteins—A Preprint, arXiv: 1903.00458v1 preprint; 2019, 13 pgs., https://arxiv.org/pdf/1903.00458.pdf.
Dalkiran, Alperen et al., ECPred: a tool for the prediction of the enzymatic functions of protein sequences based on the EC nomenclature, BMC Bioinformatics (2018) 19:334, 13 pgs.
Devlin, Jacob et al., BERT: Pre-training of Deep Bidirectional Transformers for Language Understanding, arXiv: 1810.04805; 2019, 16 pgs., https://arxiv.org/pdf/1810.04805.pdf.

(Continued)

*Primary Examiner* — Anna Skibinsky
(74) *Attorney, Agent, or Firm* — Nicholson De Vos Webster & Elliott LLP

(57) ABSTRACT

Techniques for predicting a pair of an enzyme primary sequence and a substrate, and interaction probability for the pair are described. An exemplary method includes receiving a request to predict a pair of an enzyme primary sequence and a substrate, and interaction probability for the pair; combining an enzyme vector, a substrate vector, and an interaction indication for the enzyme and substrate to form a machine learning model input; applying a machine learning model to the machine learning model input to predict the pair of an enzyme primary sequence and a substrate, and interaction probability for the pair; and outputting a result of the application of the machine learning model including the predicted pair of an enzyme primary sequence and a substrate, and interaction probability for the pair.

20 Claims, 11 Drawing Sheets

(56) References Cited

PUBLICATIONS

Dou, Jiayi et al., Sampling and energy evaluation challenges in ligand binding protein design, Protein Science; 2017, pp. 2426-2437, vol. 26, https://onlinelibrary.wiley.com/doi/epdf/10.1002/pro.3317.

Fowler, Douglas M.; Fields, Stanley, Deep mutational scanning: a new style of protein science, Nat Methods. Aug. 2014; 11(8), 17 pgs.

Fox, Naomi K. et al., SCOPe: Structural Classification of Proteins—extended, integrating SCOP and ASTRAL data and classification of new structures, Nucleic Acids Research (2013), pp. D304-D309, vol. 42, Database issue.

Hadadi, Noushin et al., Enzyme annotation for orphan and novel reactions using knowledge of substrate reactive sites, Proceedings of the National Academy of Science (PNAS); 2019, 10 pgs., https://www.pnas.org.

Hopf, Thomas A. et al., Mutation effects predicted from sequence co-variation, Nat. Biotechnol. (2017), 26 pgs.

Huang, Po-Ssu et al., The coming of age of de novo protein design, Nature, 537; Sep. 15, 2016, pp. 320-327, https://www.bakerlab.org/wp-content/uploads/2016/09/HuangBoyken_DeNovoDesign_Nature2016.pdf.

Jeske, Lisa et al., BRENDA in 2019: a European ELIXIR core data resource, Nucleic Acids Research; 2018, 8 pgs., vol. 47, https://pdfs.semanticscholar.org/c1f4/0918851e899fbdc0cdffea9f162acab67210.pdf?_ga=2.169725993.94394913.1658075614-1645612148.1658075614.

Karami, Yasaman et al., DaReUS-Loop: accurate loop modeling using fragments from remote or unrelated proteins, Scientific Reports (2018), 12 pgs.

Li, Yu et al., DEEPre: sequence-based enzyme EC number prediction by deep learning, Bioinformatics; 2017, pp. 760-769, vol. 34.

Liu; Yinhan et al., ROBERTa: A Robustly Optimized BERT Pretraining Approach, arXiv preprint arXiv:1907.11692; 2019, 13 pgs.

Lopes, Pedro E.M. et al., Current Status of Protein Force Fields for Molecular Dynamics Simulations, Molecular modeling of proteins, Ch 3. (2015), pp. 47-71.

Mizuguchi, Kenji et al., HOMSTRAD: A database of protein structure alignments for homologous families, Protein Science (1998), pp. 2469-2471.

Nguyen, Thin et al., GraphDTA: prediction of drug-target binding affinity using graph convolutional networks, bioRxiv preprint (2019), 16 pgs., https://doi.org/10.1101/684662.

Ozturk, Hakime et al., DeepDTA: Deep Drug-Target Binding Affinity Prediction, arXiv:1801.10193; 2018, 18 pgs.

Park, Hahnbeom et al., Protein Loop Modeling Using a New Hybrid Energy Function and Its Application to Modeling in Inaccurate Structural Environments, PloS One, Nov. 24, 2014, 18 pgs.

Petrovic, Dusan et al., Conformational dynamics and enzyme evolution, J. R. Soc. Interface 15; 2018, 18 pgs., http://dx.doi.org/10.1098/rsif.2018.0330.

Rao, Roshan et al., Evaluating Protein Transfer Learning with TAPE, 33rd Conference on Neural Information Processing Systems (NeurIPS), Vancouver, Canada; 2019, 13 pgs., https://papers.nips.cc/paper/2019/file/37f65c068b7723cd7809ee2d31d7861c-Paper.pdf.

Riesselman, Adam et al., Accelerating Protein Design Using Autoregressive Generative Models, bioRxiv preprint; 2019, 7 pgs., https://www.biorxiv.org/content/10.1101/757252v1.full.pdf.

Riesselman, Adam J.; Ingraham, John B.; Marks, Debora S., Deep generative models of genetic variation capture mutation effects, Nat Methods; 2018, 25 pgs., https://arxiv.org/ftp/arxiv/papers/1712/1712.06527.pdf.

Rives, Alexander et al., Biological Structure and Function Emerge From Scaling Unsupervised Learning to 250 Million Protein Sequences, bioRxiv preprint; 2019, 25 pgs., https://doi.org/10.1101/622803.

Romero, Philip A.; Arnold, Frances H., Exploring protein fitness landscapes by directed evolution, Nat Rev Mol Cell Biol, 10; Dec. 2009, 25 pgs., https://authors.library.caltech.edu/16942/3/nihms251972.pdf.

Ryu, Jae Yong et al., Deep learning enables high-quality and high-throughput prediction of enzyme commission numbers Proceedings of the National Academy of Sciences (PNAS); Jul. 9, 2019, pp. 13996-14001, vol. 116/ No. 28.

Strodthoff, Nils et al., UDSMProt: Universal Deep Sequence Models for Protein Classification, bioRxiv preprint; 2019, 11 pgs., https://doi.org/10.1101/704874.

Tian, Siyang et al., CypReact: A Software Tool for in silico Reactant Prediction for Human Cytochrome P450 Enzymes, J. Chem. Inf. Model. 58; 2018, pp. 1282-1291.

Vaswani, Ashish et al., Attention Is All You Need, 31st Conference on Neural Information Processing Systems (NIPS), Long Beach, CA;; 2017, 15 pgs.

Wang, Jingxue et al., Computational Protein Design with Deep Learning Neural Networks, Scientific reports, 16 pgs., vol. 8, https://arxiv.org/ftp/arxiv/papers/1801/1801.07130.pdf.

Wrenbeck, Emily E. et al., Single-mutation fitness landscapes for an enzyme on multiple substrates reveal specificity is globally encoded, Nature Communications, 8:15695; 2017, 10 pgs.

Wu, Zachary et al., Machine learning-assisted directed protein evolution with combinatorial libraries, Proceedings of the National Academy of Sciences (PNAS); Apr. 30, 2019, pp. 8852-8858, vol. 116 /No. 18.

Yang, Kevin K. et al., Machine learning-guided directed evolution for protein engineering, arXiv:1811.10775; Apr. 19, 2019, 15 pgs.

Yu, Jiahui et al., Generative Image Inpainting with Contextual Attention, Proceedings of the IEEE Conference on Computer Vision and Pattern Recognition (2018), 15 pgs., https://arxiv.org/pdf/1801.07892.pdf.

Zanger, Ulrich M.; Schwab, Matthias, Cytochrome P450 enzymes in drug metabolism: Regulation of gene expression, enzyme activities, and impact of genetic variation, Pharmacology & Therapeutics (2013), pp. 103-141, vol. 138.

Final Office Action, U.S. Appl. No. 16/896,907, dated Aug. 1, 2023, 13 pages.

Notice of Allowance, U.S. Appl. No. 16/896,907, dated Oct. 17, 2023, 9 pages.

\* cited by examiner

SYSTEMS, METHODS, AND APPARATUSES TO PREDICT PAIRS OF ENZYME PRIMARY SEQUENCES AND SUBSTRATES AND AN INTERACTION PROBABILITY FOR EACH PREDICTED PAIR

BACKGROUND

Enzymes are biologically encoded and synthesized as a linear chain of amino acids, of which there are 20 canonical members. This linear chain then folds into a dynamic 3D structure to accomplish its biological purpose. As the enzyme class responsible for controlling all biochemical reactions, enzymes serve a variety of functions.

Enzymes have been engineered by nature to accomplish the reactions necessary for life. To adapt these enzyme catalysts to human tasks, directed evolution has emerged as a simple yet powerful tool that mirrors natural optimization with high success. However, directed evolution of functional enzyme is heavily dependent on the identification of a suitable starting point, or a parent enzyme with a measurable level of starting activity. While domain experts supplemented by serendipity have developed the intuition necessary for identifying this parent enzyme for specific reactions, engineering enzymes with novel functionality from scratch remains a fundamental challenge.

BRIEF DESCRIPTION OF DRAWINGS

Various embodiments in accordance with the present disclosure will be described with reference to the drawings, in which.

DETAILED DESCRIPTION

The present disclosure relates to methods, apparatus, systems, and non-transitory computer-readable storage media for predicting one or more pairs of enzyme and substrate combinations and an interaction probability per predicated pair. In particular, aspects of an incomplete enzyme and/or incomplete substrate can be predicted.

Predicting new substrates for a given enzyme has potential applications in developing drug discovery panels (2), understanding enzymatic promiscuity (3), designing metabolic pathways (4), and combating antibiotic resistance (5). Predicting whether an enzyme and substrate exhibit activity has potential applications in bio-orthogonal chemistry and gene annotation. Detailed herein is a machine learning model for enzyme-substrate pairs that is able to predict possible amino acid mutations in a given enzyme, alterations to functional groups in a given substrate, and an interaction probability between the enzyme-substrate pairs that assesses how likely they are to interact.

To compare these heterogeneous data types (enzymes and substrates), the machine learning model is a multi-headed self-attention model (e.g., a trained transformer-base model) that intakes three components that are jointly combined. In particular, the machine learning model intakes a vectors representing: 1) a enzyme representation of enzymes by their primary sequence (e.g., an embedding for each of the 25 amino acids (including non-canonicals)); a substrate representation of small molecule substrates (e.g., an embedding of a substrate); and 3) an interaction flag which is a binary variable describing if the enzyme and substrate are known to interact. As such, each input component of the enzymatic system, the enzyme, substrate, and flag, are embedded in some manner with the identical number of hidden dimensions. These embedded vectors are then passed through 6 layers of self-attention such as implemented in a transformer encoder and a final linear layer to make the final token predictions for each respective portion. Negative examples can be generated by randomly shuffling enzyme-substrate pairs in the input, breaking their physicochemical relationship.

Figure 1:
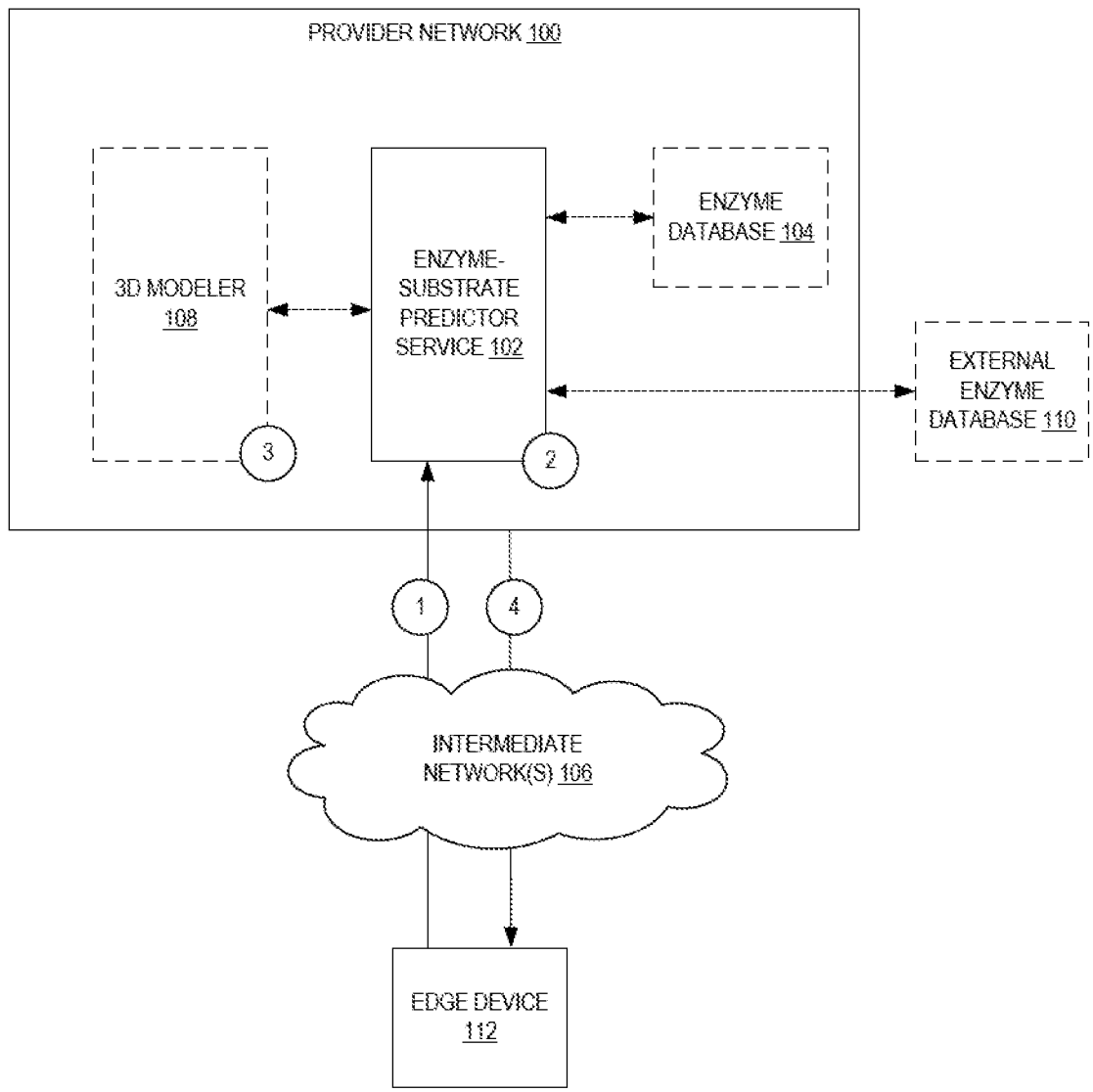
FIG. 1 illustrates embodiments of a system to predict one or more pairs of enzyme primary sequences and substrates, and an interaction probability for each predicted pair.

FIG. 1 illustrates embodiments of a system to predict one or more pairs of enzyme primary sequences and substrates, and an interaction probability for each predicted pair. As shown, an enzyme-substrate predictor service 102 predicts, according to a request, one or more pairs of enzyme and substrate combinations and an interaction probability per predicated pair from an incomplete enzyme and/or an incomplete substrate using one or more trained machine learning models. Details of how this is accomplished are discussed in more detail below.

A request may include a representation of a primary sequence of a enzyme, a representation of a substrate composition, and an indication of reactivity of the substrate and the enzyme. In some embodiments, representations in a format does not require further processing by the enzyme-substrate predictor service 102. In other embodiments, the enzyme-substrate predictor service 102 processes the representations to be in a format expected by the one or more models.

A provider network 100 (or, "cloud" provider network) provides users with the ability to utilize one or more of a variety of types of computing-related resources such as compute resources (e.g., executing virtual machine (VM) instances and/or containers, executing batch jobs, executing code without provisioning servers), data/storage resources (e.g., object storage, block-level storage, data archival storage, databases and database tables, etc.), network-related resources (e.g., configuring virtual networks including groups of compute resources, content delivery networks (CDNs), Domain Name Service (DNS)), application resources (e.g., databases, application build/deployment services), access policies or roles, identity policies or roles, machine images, routers and other data processing resources, etc. These and other computing resources may be provided as services, such as a hardware virtualization service that can execute compute instances, a storage service that can store data objects, etc. The users (or "customers") of provider networks 100 may utilize one or more user accounts that are associated with a customer account, though these terms may be used somewhat interchangeably depending upon the context of use. Users may interact with a provider network 100 across one or more intermediate networks 106 (e.g., the internet) via one or more interface(s), such as through use of application programming interface (API) calls, via a console implemented as a website or application, etc. An API refers to an interface and/or communication protocol between a client and a server, such that if the client makes a request in a predefined format, the client should receive a response in a specific format or initiate a defined action. In the cloud provider network context, APIs provide a gateway for customers to access cloud infrastructure by allowing customers to obtain data from or cause actions within the cloud provider network, enabling the development of applications that interact with resources and services hosted in the cloud provider network. APIs can also enable different services of the cloud provider network to exchange data with one another. The interface(s) may be part of, or serve as a front-end to, a control plane of the provider network 100 that includes "backend" services supporting and enabling the services that may be more directly offered to customers.

For example, a cloud provider network (or just "cloud") typically refers to a large pool of accessible virtualized computing resources (such as compute, storage, and networking resources, applications, and services). A cloud can provide convenient, on-demand network access to a shared pool of configurable computing resources that can be programmatically provisioned and released in response to customer commands. These resources can be dynamically provisioned and reconfigured to adjust to variable load. Cloud computing can thus be considered as both the applications delivered as services over a publicly accessible network (e.g., the Internet, a cellular communication network) and the hardware and software in cloud provider data centers that provide those services.

To provide these and other computing resource services, provider networks 100 often rely upon virtualization techniques. For example, virtualization technologies may be used to provide users the ability to control or utilize compute instances (e.g., a VM using a guest operating system (O/S) that operates using a hypervisor that may or may not further operate on top of an underlying host O/S, a container that may or may not operate in a VM, an instance that can execute on "bare metal" hardware without an underlying hypervisor), where one or multiple compute instances can be implemented using a single electronic device. Thus, a user may directly utilize a compute instance (e.g., provided by a hardware virtualization service) hosted by the provider network to perform a variety of computing tasks. Additionally, or alternatively, a user may indirectly utilize a compute instance by submitting code to be executed by the provider network (e.g., via an on-demand code execution service), which in turn utilizes a compute instance to execute the code typically without the user having any control of or knowledge of the underlying compute instance(s) involved.

For example, in various embodiments, a "serverless" function may include code provided by a user or other entity—such as the provider network itself—that can be executed on demand Serverless functions may be maintained within provider network 100 by an on-demand code execution service and may be associated with a particular user or account or be generally accessible to multiple users/accounts. A serverless function may be associated with a Uniform Resource Locator (URL), Uniform Resource Identifier (URI), or other reference, which may be used to invoke the serverless function. A serverless function may be executed by a compute instance, such as a virtual machine, container, etc., when triggered or invoked. In some embodiments, a serverless function can be invoked through an application programming interface (API) call or a specially formatted HyperText Transport Protocol (HTTP) request message. Accordingly, users can define serverless functions that can be executed on demand, without requiring the user to maintain dedicated infrastructure to execute the serverless function. Instead, the serverless functions can be executed on demand using resources maintained by the provider network 100. In some embodiments, these resources may be maintained in a "ready" state (e.g., having a pre-initialized runtime environment configured to execute the serverless functions), allowing the serverless functions to be executed in near real-time.

In some embodiments, the provider network 100 includes an enzyme database 104 which includes substrate/enzyme information used for training the model(s) of the enzyme-substrate predictor service 102. For example, a BRENDA type database is stored. In some embodiments, the provider network 100 communicates with an external enzyme database 110 (such as BRENDA) which includes substrate/enzyme information used for training the model(s) of the enzyme-substrate predictor service 102.

In some embodiments, a 3-D modeler 108 allows for a predicted pair to have a 3-D representation generated.

Circles with numbers in them indicate an exemplary flow using the enzyme-substrate predictor service 102. A circle 1, an edge device 112 sends a request for an enzyme/substrate pair prediction. The enzyme-substrate predictor service 102 processes this request at circle 2. In this example, a 3-D representation is generated from the predication at circle 3.

The predication and 3-D representation are returned to the requester at circle 4.

Figure 2:
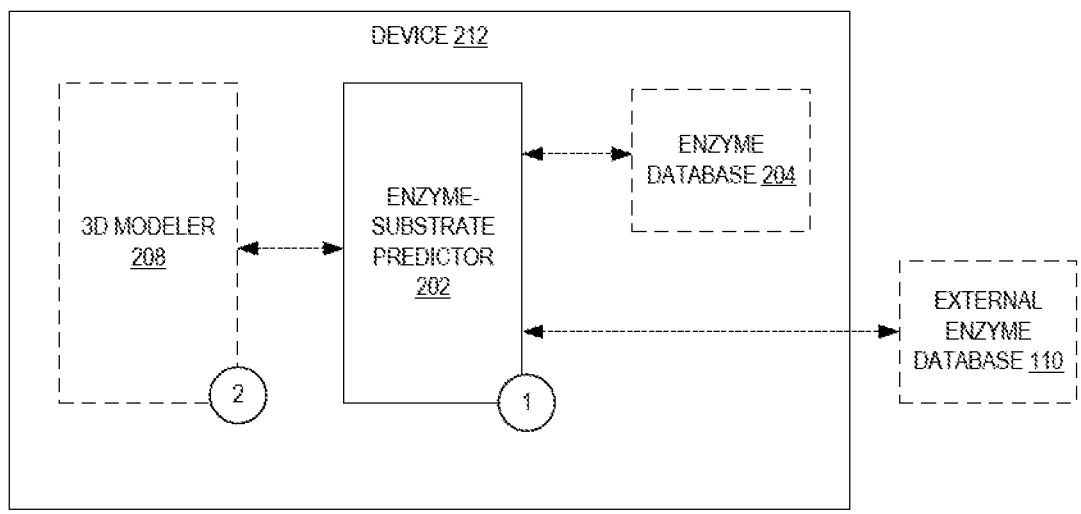
FIG. 2 illustrates embodiments of a device to predict one or more pairs of enzyme primary sequences and substrates, and an interaction probability for each predicted pair.

FIG. 2 illustrates embodiments of a device to predict one or more pairs of enzyme primary sequences and substrates, and an interaction probability for each predicted pair. As shown, an enzyme-substrate predictor 202 predicts, according to a request, one or more pairs of enzyme and substrate combinations and an interaction probability per predicated pair from an incomplete enzyme and/or an incomplete substrate using one or more trained machine learning models. Details of how this is accomplished are discussed in more detail below.

A request may include a representation of a primary sequence of a enzyme, a representation of a substrate composition, and an indication of reactivity of the substrate and the enzyme. In some embodiments, representations in a format does not require further processing by the enzyme-substrate predictor 202. In other embodiments, the enzyme-substrate predictor 202 processes the representations to be in a format expected by the one or more models.

In some embodiments, the device 212 includes an enzyme database 204 which includes substrate/enzyme information used for training the model(s) of the enzyme-substrate predictor 202. For example, a BRENDA type database is stored. In some embodiments, the device 212 network 100 communicates with an external enzyme database 110 (such as BRENDA) which includes substrate/enzyme information used for training the model(s) of the enzyme-substrate predictor 202.

In some embodiments, a 3-D modeler 208 allows for a predicted pair to have a 3-D representation generated.

a chain. In some embodiments, the amino acids of the chain are represented using one-letter amino acid codes or their three-letter equivalents. Table I below illustrates an example of amino acid representations that conform to International Union of Pure and Applied Chemistry usage.

TABLE I

| Symbol | 3-letter | Meaning | Codons | IUB Depiction |
|---|---|---|---|---|
| A | Ala | Alanine | GCT, GCC, GCA, GCG | !GCX |
| B | Asp, Asn | Aspartic, Asparagine | GAT, GAC, AAT, AAC | !RAY |
| C | Cys | Cysteine | TGT, TGC | !TGY |
| D | Asp | Aspartic | GAT, GAC | !GAY |
| E | Glu | Glutamic | GAA, GAG | !GAR |
| F | Phe | Phenylalanine | TTT, TTC | !TTY |
| G | Gly | Glycine | GGT, GGC, GGA, GGG | !GGX |
| H | His | Histidine | CAT, CAC | !CAY |
| I | Ile | Isoleucine | ATT, ATC, ATA | !ATH |
| K | Lys | Lysine | AAA, AAG | !AAR |
| L | Leu | Leucine | TTG, TTA, CTT, CTC, CTA, CTG !TTR, CTX, YTR; YTX | |
| M | Met | Methionine | ATG | !ATG |
| N | Asn | Asparagine | AAT, AAC | !AAY |
| P | Pro | Proline | CCT, CCC, CCA, CCG | !CCX |
| Q | Gln | Glutamine | CAA, CAG | !CAR |
| R | Arg | Arginine | CGT, CGC, CGA, CGG, AGA, AGG !CGX, AGR, MGR; MGX | |
| S | Ser | Serine | TCT, TCC, TCA, TCG, AGT, AGC | !TCX, AGY; WSX |
| T | Thr | Threonine | ACT, ACC, ACA, ACG | !ACX |
| V | Val | Valine | GTT, GTC, GTA, GTG | !GTX |
| W | Trp | Tryptophan | TGG | !TGG |
| X | Xxx | Unknown | | !XXX |
| Y | Tyr | Tyrosine | TAT, TAC | !TAY |
| Z | Glu, Gln | Glutamic, Glutamine | GAA, GAG, CAA, CAG | !SAR |
| * | End | Terminator | TAA, TAG, TGA | !TAR, TRA; TRR |

Circles with numbers in them indicate an exemplary flow using the enzyme-substrate predictor 202. A circle 1, the enzyme-substrate predictor 202 processes a request. In this example, a 3-D representation is generated from the predication at circle 2.

Figure 3:
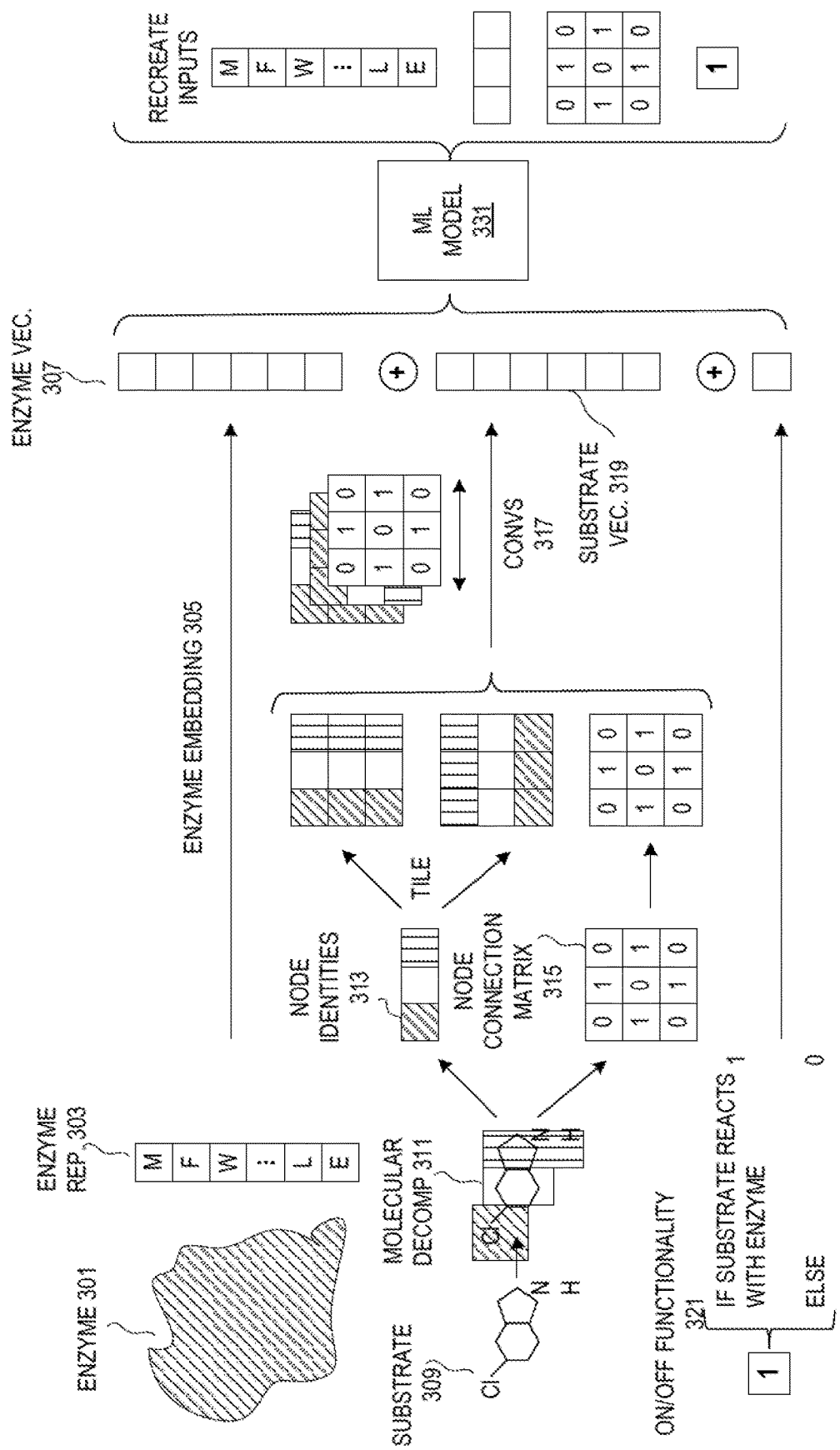
FIG. 3 illustrates an example of a diagram of a flow of acts to generate a prediction of a pair of an enzyme and a substrate, and an interaction between the predicted pair.

FIG. 3 illustrates an example of a diagram of a flow of acts to generate a prediction of a pair of an enzyme and a substrate, and an interaction between the predicted pair. This generation is based on an enzyme 301, a substrate 309, and an on/off functionality 321 indicating if the substrate 309 interactS with the enzyme 301.

As shown, an enzyme 301 is represented in a character-based format shown as enzyme representation 303. The enzyme representation 303 is the primary sequence of an enzyme which is a group of amino acids linked together in A learned enzyme embedding 305 is applied to the enzyme representation 303 to generate an enzyme vector 307.

The chemical representation of the substrate 309 is decomposed into molecular decomposition 311. In some embodiments, the molecular decomposition represents the molecule substrates as a connection graph formed by tree decomposition. The graph is embedded as a 2D node connection matrix 315 with 1D embeddings for each node. These 1D embeddings are then tiled using node identities (chemical reference or group) 313 for each node in both the vertical and horizontal directions, to form two 2D representations for each node. These 2D representations are then stacked with the 2D connection matrix and the stacked channels are upsampled to the hidden dimension of an attention sequence (e.g., of the machine learning model 331 which may be attention-based such as a transformer-based model). The result of the upsampling is convolved down to a 1D with a series of convolutions 317 to form a substrate vector 319.

The enzyme vector 307, substrate vector 319, and on/off functionality 321 are combined (e.g., concatenated) and fed to a model 331 to generate a representative enzyme and substrate (the pair detailed above) and an indication of reactivity. The model 331, in some embodiments, is a transformer-based model. The pairs and reactivity may be used to generate a 3-D representation of the resulting enzyme.

In some embodiments, the model 331 is trained using self-supervised input recovery tasks coupled to a multi-task loss function. In some embodiments, training data is obtained by parsing an enzyme information data base (e.g., an enzyme information service's (e.g., BRENDA's) text format releases). BRENDA categorizes enzyme information by EC number (example: EC 1.1.1.1). From these records, the enzyme, substrate/product, and natural substrate/product lines are extracted. Within each BRENDA record, each enzyme is matched to each substrate by a enzyme identifier unique to that record. For substrates, common names are extracted from substrate lines. For lines containing the r reversibility tag, the labeled products are extracted as substrates. Otherwise, only the substrates are extracted from each reaction line.

From these functional pairs, match of the set of available enzymes is made against the set of available substrates. If the enzyme-substrate pair does not already exist as a functional pair, this is specified as nonfunctional to augment the dataset of functional enzyme—substrate pairs.

In some embodiments, during training a random amount of the input enzymes are removed and replaced with a <MASK> token. At the start of training, an equal amount of data for nonfunctional enzyme—substrate pairs is generated by randomly pairing enzymes and substrates present in the enzyme information.

In some embodiments, a four-part loss function that uses cross-entropy is used to fit a sequence recovery task on the enzyme $L_{prot}$, the molecular adjacency matrix $L_{mat}$, the molecular node identity recovery task on the substrate $L_{nodes}$, and the prediction of substrate-enzyme functionality $L_{func}$. The final total loss is a weighted summation of the individual cross entropy losses. With the exception of $L_{func}$, each individual loss component is roughly scaled to the starting training loss of the enzyme loss by scaling $L_{mat}$ up by 10-fold.

Figure 4:
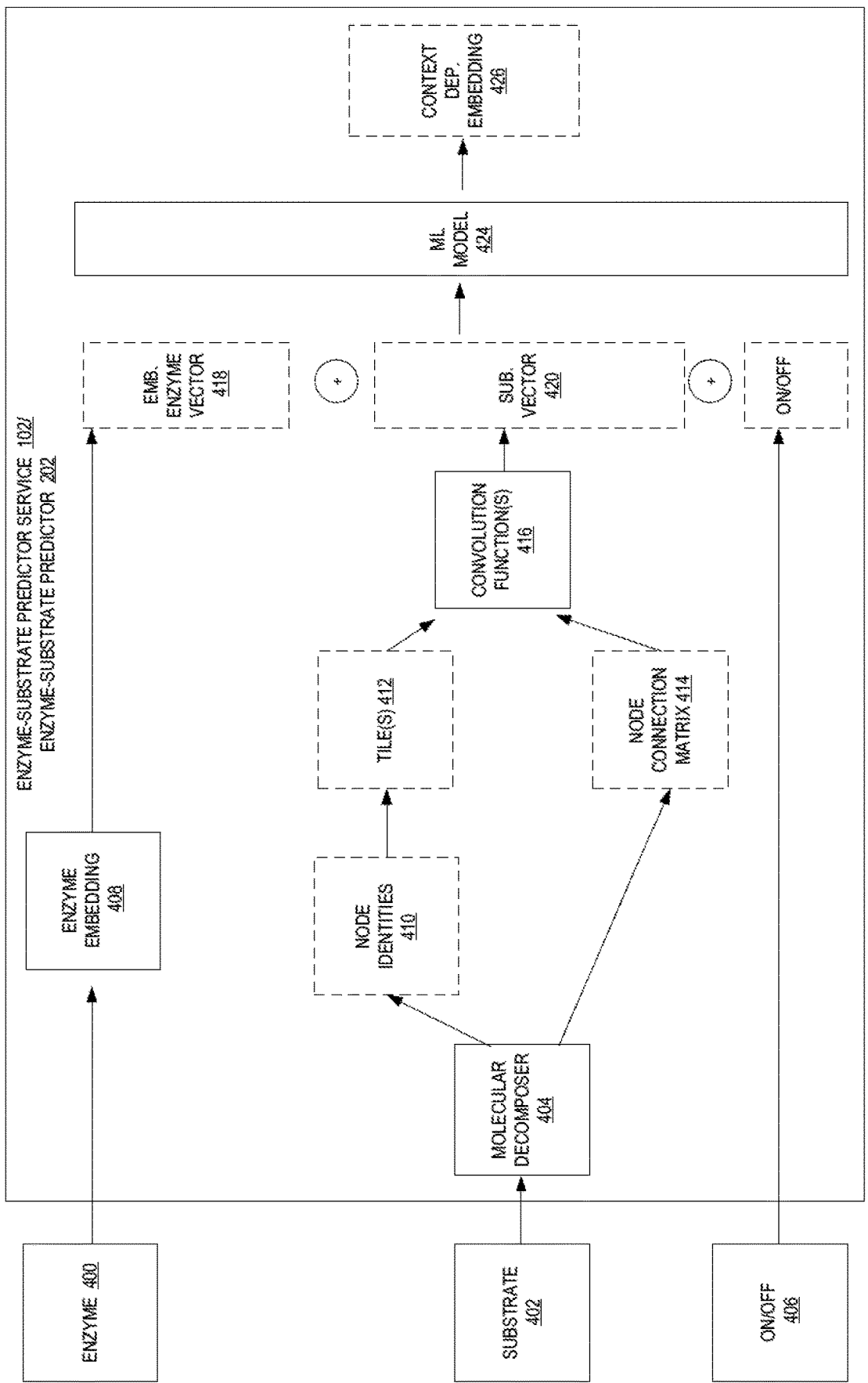
FIG. 4 illustrates embodiments of an enzyme-substrate predictor or enzyme-substrate predictor service.

FIG. 4 illustrates embodiments of an enzyme-substrate predictor or enzyme-substrate predictor service. In particular, embodiments of the enzyme-substrate predictor service 102 or enzyme-substrate predictor 202 are shown. In this illustration, aspects shown in dotted lines are data structures that change depending on the input.

As shown, inputs into the enzyme-substrate predictor service 102 or enzyme-substrate predictor 202 include an enzyme representation 400, a substrate representation 402, and an on/off indicator 406. An enzyme embedding 408 takes in the enzyme representation and generates an enzyme vector 418.

The substrate representation 402 is molecularly decomposed using molecular decomposer 404 into node identities 410 (and then into tiles 412) and a node connection matrix 414 as detailed above. One or more convolution functions 416 are then applied to the tiles 412 and node connection matrix 414 as detailed above to generate a substrate vector 420.

The enzyme vector 418, the substrate vector 420, and on/off indication 406 are combined (e.g., concatenated) to form an input for the machine learning model 424 (e.g., a joint attention model, a long short term memory, a convolutional neural network model, etc.) to generate a representative enzyme and substrate (the pair detailed above) and an indication of reactivity. The model 424, in some embodiments, is a transformer-based model. In some embodiments, the output of the ML model 424 is a context dependent embedding 426 that uses functionality context (predictions). The pairs and reactivity may be used to generate a 3-D representation of the resulting enzyme.

Figure 5:
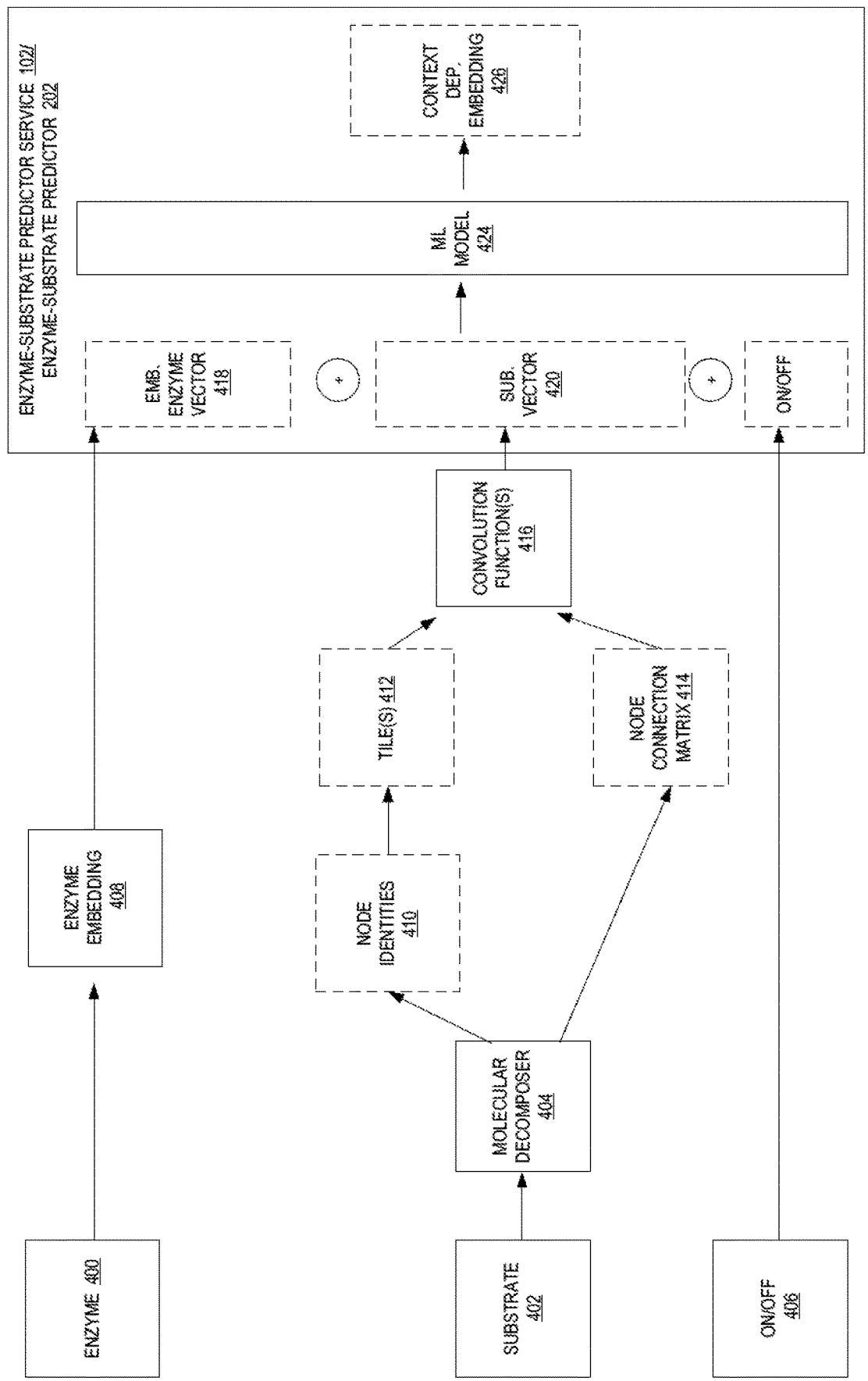
FIG. 5 illustrates embodiments of an enzyme-substrate predictor or enzyme-substrate predictor service.

FIG. 5 illustrates embodiments of an enzyme-substrate predictor or enzyme-substrate predictor service. In particular, embodiments of the enzyme-substrate predictor service 102 or enzyme-substrate predictor 202 are shown. In this illustration, aspects shown in dotted lines are data structures that change depending on the input. This version of the enzyme-substrate predictor service 102 or enzyme-substrate predictor 202 does not include any of the data preparation components for the input into the machine learning model 424. Rather that preparation has been performed external to the enzyme-substrate predictor service 102 or enzyme-substrate predictor 202.

As shown, an enzyme representation 400, a substrate representation 402, and an on/off indicator 406 are still the basis of the input into the model. An enzyme embedding 408 takes in the enzyme representation and generates an enzyme vector 418.

The substrate representation 402 is molecularly decomposed using molecular decomposer 404 into node identities 410 (and then into tiles 412) and a node connection matrix 414 as detailed above. One or more convolution functions 416 are then applied to the tiles 412 and node connection matrix 414 as detailed above to generate a substrate vector 420.

The enzyme vector 418, the substrate vector 420, and on/off indication 406 are combined (e.g., concatenated) to form an input for the machine learning model 424 to generate a representative enzyme and substrate (the pair detailed above) and an indication of reactivity. This combination may be done in the enzyme-substrate predictor service 102 or enzyme-substrate predictor 202 or outside. As noted, the ML model 424, in some embodiments, is a transformer-based model. In some embodiments, the output of the ML model 424 is a context dependent embedding 426 that uses functionality context (predictions). The pairs and reactivity may be used to generate a 3-D representation of the resulting enzyme.

Figure 6:
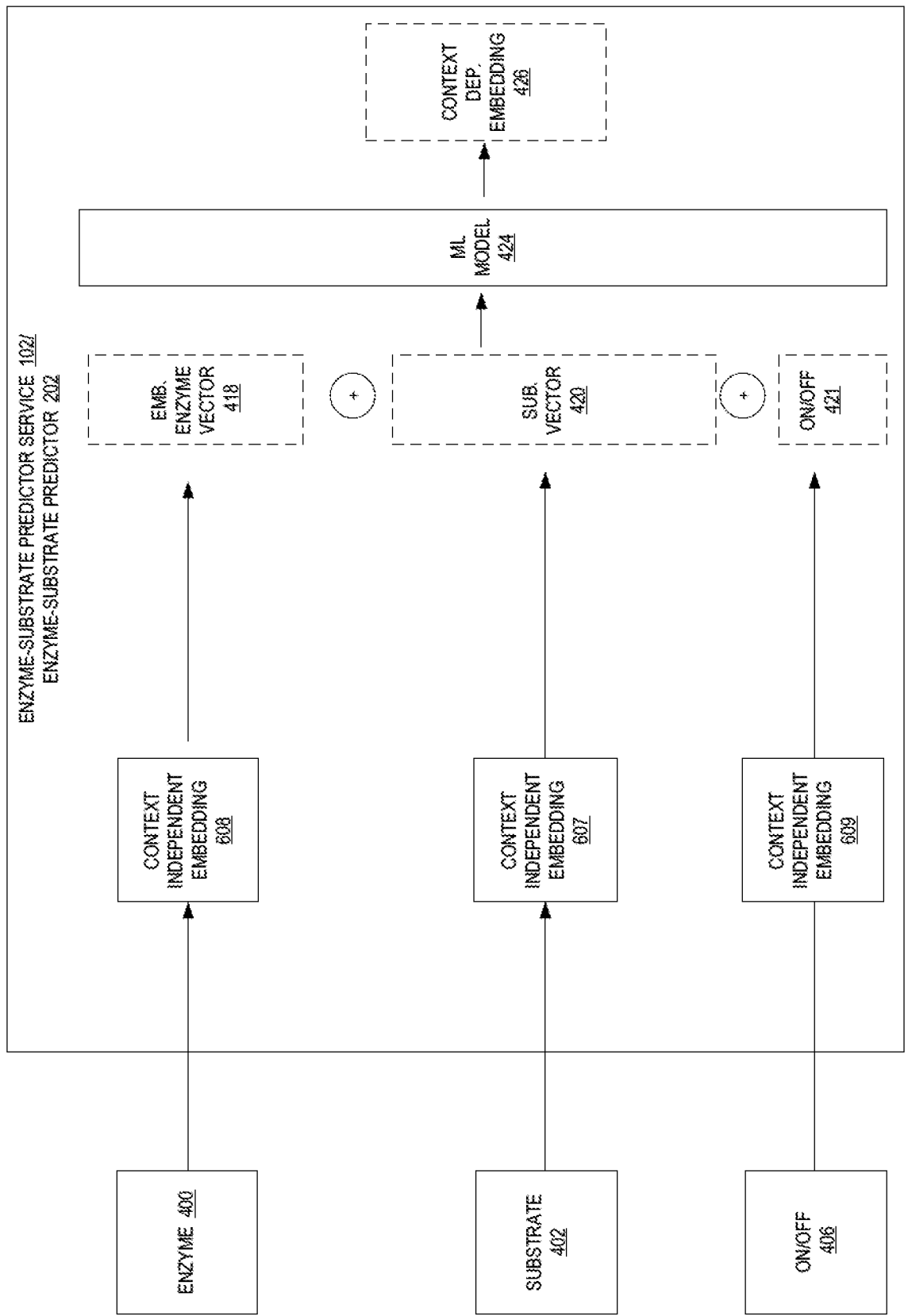
FIG. 6 illustrates embodiments of an enzyme-substrate predictor or enzyme-substrate predictor service.

FIG. 6 illustrates embodiments of an enzyme-substrate predictor or enzyme-substrate predictor service. In particular, embodiments of the enzyme-substrate predictor service 102 or enzyme-substrate predictor 202 are shown. In this illustration, aspects shown in dotted lines are data structures that change depending on the input. T As shown, an enzyme representation 400, a substrate representation 402, and an on/off indicator 406 are still the basis of the input into the model. Each of them is subjected to a corresponding context independent embedding 607-609 to generate an enzyme vector 418, substrate vector 420, and an on/off vector 421.

The enzyme vector 418, the substrate vector 420, and on/off indication vector 421 are combined (e.g., concatenated) to form an input for the machine learning model 424 to generate a representative enzyme and substrate (the pair detailed above) and an indication of reactivity. This combination may be done in the enzyme-substrate predictor service 102 or enzyme-substrate predictor 202 or outside. As noted, the ML model 424, in some embodiments, is a transformer-based model. In some embodiments, the output of the ML model 424 is a context dependent embedding 426 that uses functionality context (predictions). The pairs and reactivity may be used to generate a 3-D representation of the resulting enzyme.

Figure 7:
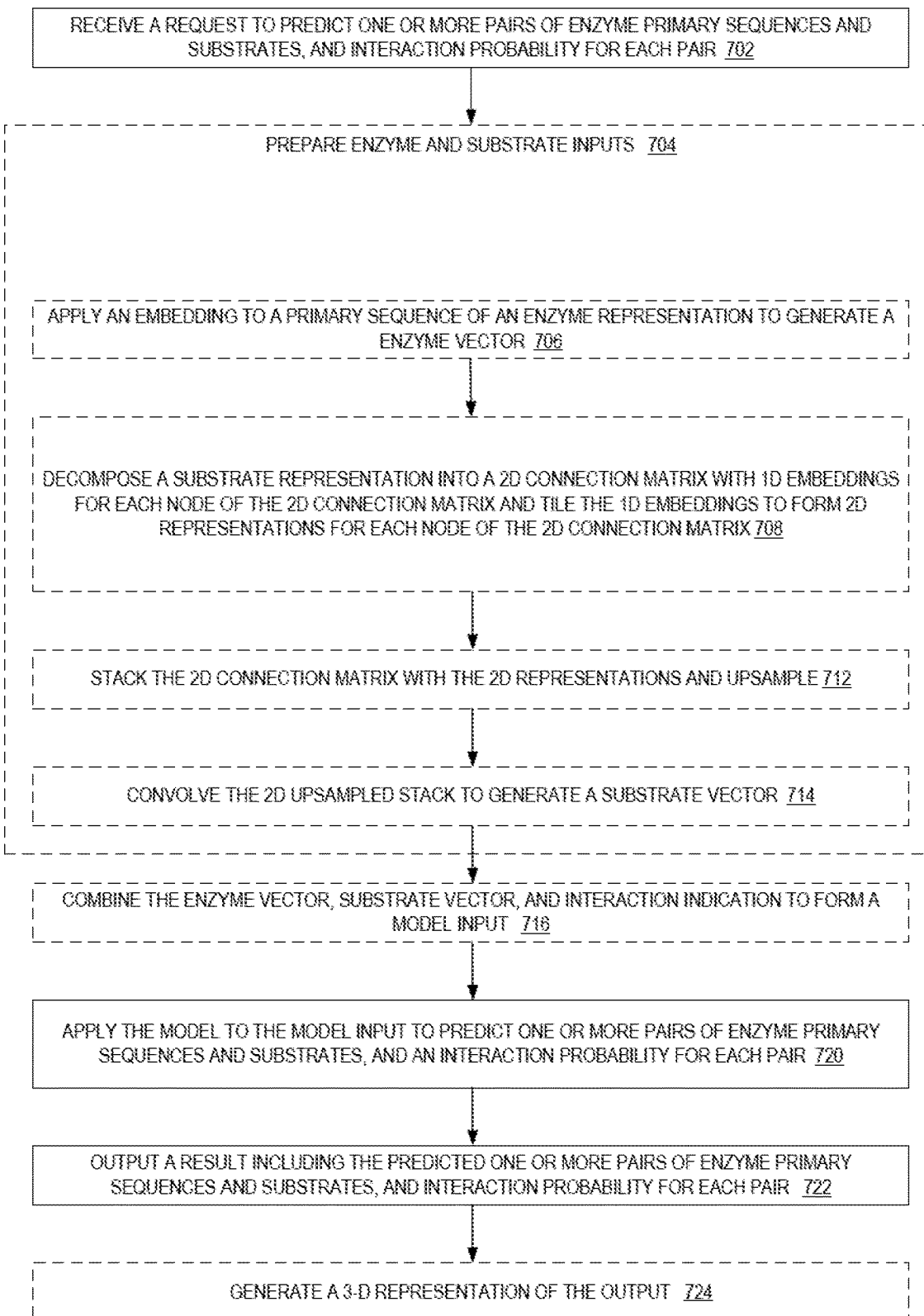
FIG. 7 is a flow diagram illustrating operations of a method for predict one or more pairs of enzyme primary sequences and substrates, and interaction probability for each pair according to some embodiments.

FIG. 7 is a flow diagram illustrating operations of a method for predict one or more pairs of enzyme primary sequences and substrates, and interaction probability for each pair according to some embodiments. Some or all of the operations (or other processes described herein, or variations, and/or combinations thereof) are performed under the control of one or more computer systems configured with executable instructions and are implemented as code (e.g., executable instructions, one or more computer programs, or one or more applications) executing collectively on one or more processors, by hardware or combinations thereof. The code is stored on a computer-readable storage medium, for example, in the form of a computer program comprising instructions executable by one or more processors. The computer-readable storage medium is non-transitory. In some embodiments, one or more (or all) of the operations are performed by the enzyme-substrate predictor service 102 or enzyme-substrate predictor 202 of the other figures.

At 702 a request to predict one or more pairs of enzyme primary sequences and substrates, and interaction probability for each pair is received.

In some embodiments, enzyme and substrate inputs are prepped at 704. This preparation may include multiple acts depending on the implementation. In some embodiments, an embedding is applied to a primary sequence of an enzyme (represented as characters) to generate an enzyme vector at 706.

In some embodiments, at 708, a substrate representation is decomposed into a 2D connection matrix with 1D embeddings for each node of the 2D connection matrix and the 1D embeddings are tiled to form 2D representations for each node of the 2D connection matrix.

In some embodiments, the 2D connection matrix is stacked with the 2D representations and upsampled at 712. In some embodiments, the 2D upsampled stack is convolved one or more times to generate a substrate vector at 714.

In some embodiments, the enzyme vector, substrate vector, and interaction indication are combined to form a model input at 716. In some embodiments, the model is a joint attention model such as a transformer-based model.

The model is applied to the model input to predict one or more pairs of enzyme primary sequences and substrates, and an interaction probability for each pair at 720.

At 722, a result including the predicted one or more pairs of enzyme primary sequences and substrates, and interaction probability for each pair is output from the model. In some embodiments, a 3D representation of the output is made at 724.

Figure 8:
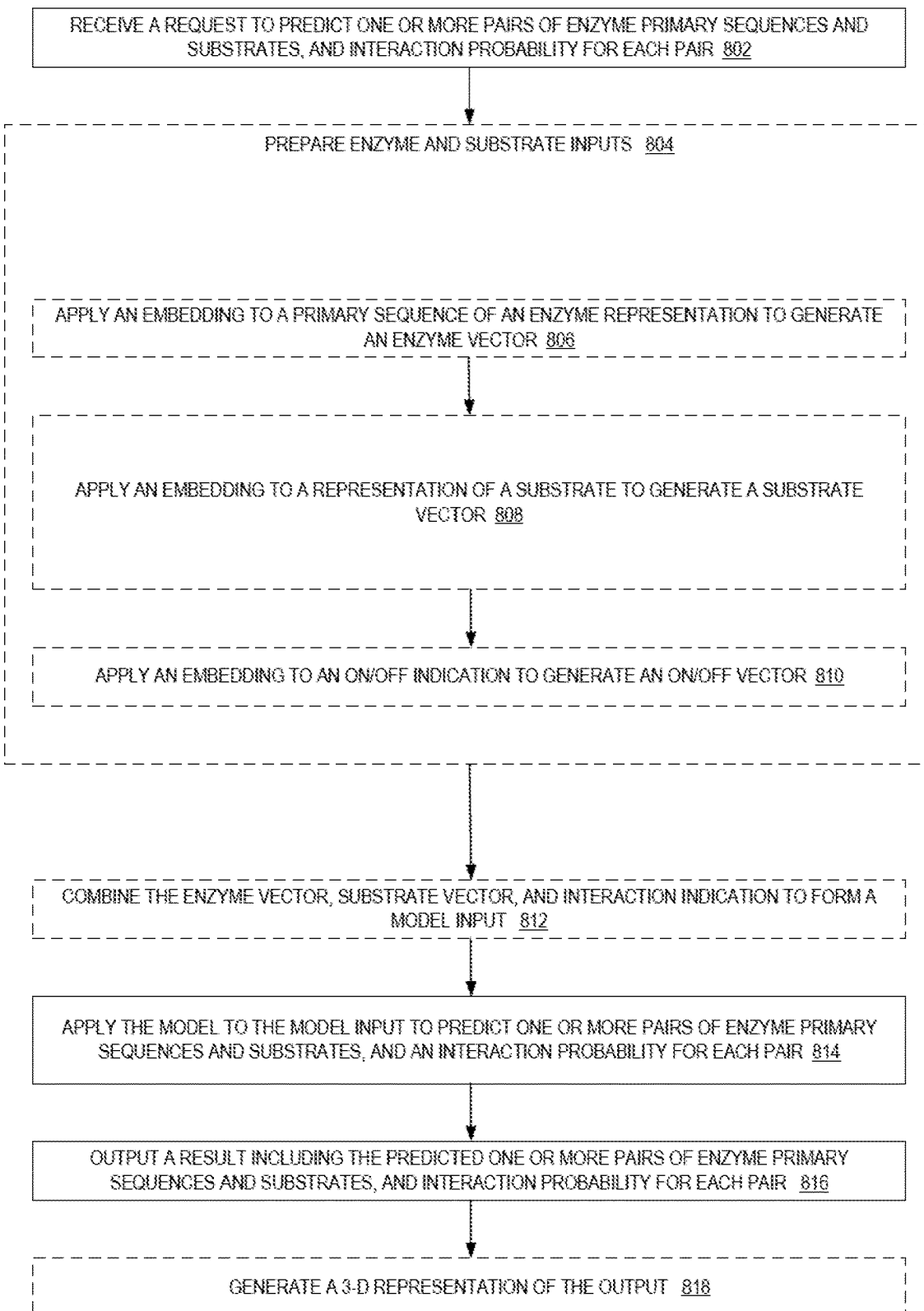
FIG. 8 is a flow diagram illustrating operations of a method for predict one or more pairs of enzyme primary sequences and substrates, and interaction probability for each pair according to some embodiments.

FIG. 8 is a flow diagram illustrating operations of a method for predict one or more pairs of enzyme primary sequences and substrates, and interaction probability for each pair according to some embodiments. Some or all of the operations (or other processes described herein, or variations, and/or combinations thereof) are performed under the control of one or more computer systems configured with executable instructions and are implemented as code (e.g., executable instructions, one or more computer programs, or one or more applications) executing collectively on one or more processors, by hardware or combinations thereof. The code is stored on a computer-readable storage medium, for example, in the form of a computer program comprising instructions executable by one or more processors. The computer-readable storage medium is non-transitory. In some embodiments, one or more (or all) of the operations are performed by the enzyme-substrate predictor service 102 or enzyme-substrate predictor 202 of the other figures.

At 802 a request to predict one or more pairs of enzyme primary sequences and substrates, and interaction probability for each pair is received.

In some embodiments, enzyme and substrate inputs are prepped at 804. This preparation may include multiple acts depending on the implementation. In some embodiments, an embedding is applied to the primary sequence of an enzyme (represented as characters) to generate an enzyme vector at 806. In some embodiments, an embedding is applied to a representation of a substrate to generate a substrate vector at 808. In some embodiments, an embedding is applied to an on/off indication to generate an on/off vector at 810.

In some embodiments, the enzyme vector, substrate vector, and interaction indication are combined to form a model input at 812. In some embodiments, the model is a joint attention model such as a transformer-based model.

The model is applied to the model input to predict one or more pairs of enzyme primary sequences and substrates, and an interaction probability for each pair at 814.

At 816, a result including the predicted one or more pairs of enzyme primary sequences and substrates, and interaction probability for each pair is output from the model. In some embodiments, a 3D representation of the output is made at 818.

Figure 9:
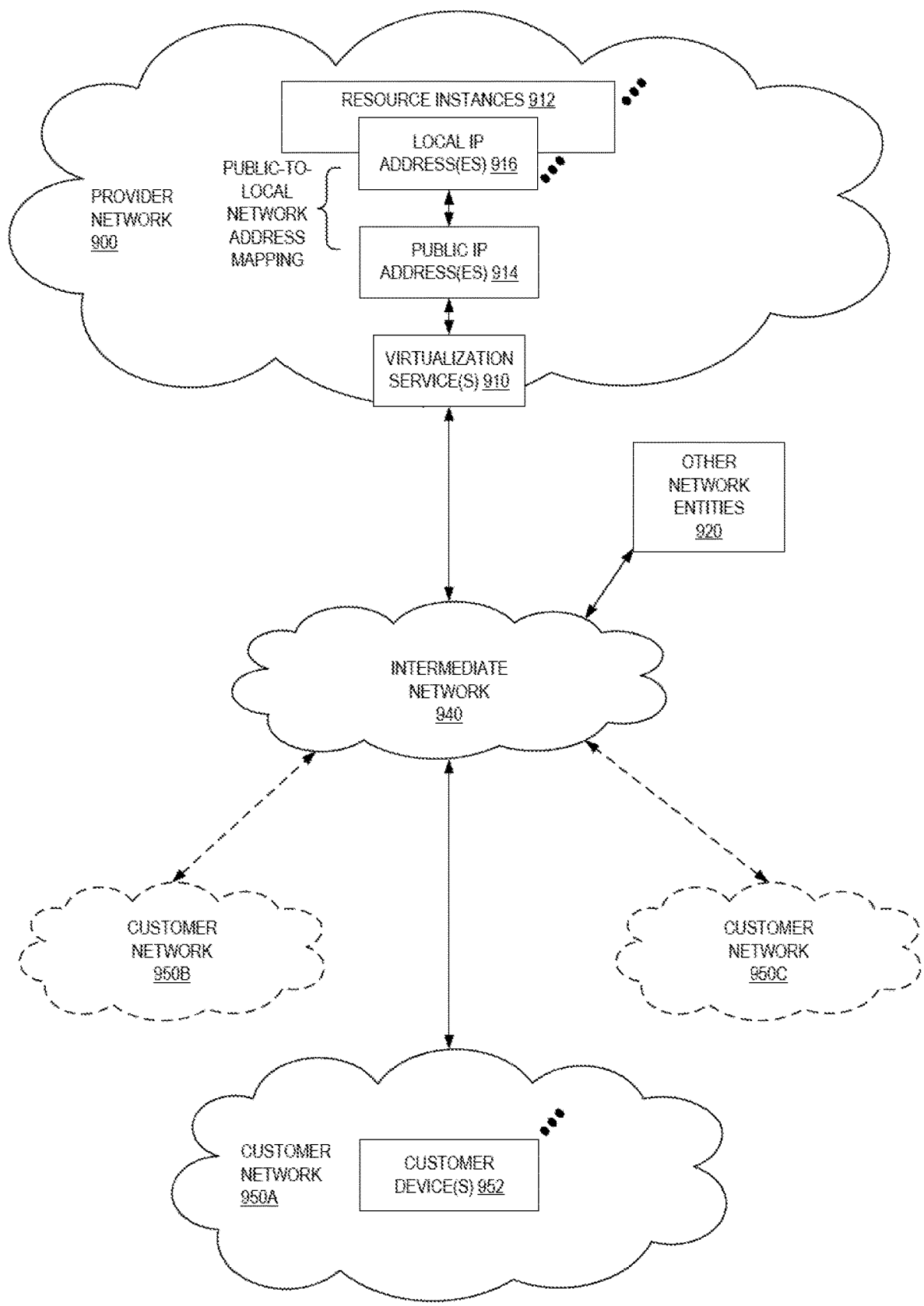
FIG. 9 illustrates an example provider network environment according to some embodiments.

FIG. 9 illustrates an example provider network (or "service provider system") environment according to some embodiments. A provider network 900 may provide resource virtualization to customers via one or more virtualization services 910 that allow customers to purchase, rent, or otherwise obtain instances 912 of virtualized resources, including but not limited to computation and storage resources, implemented on devices within the provider network or networks in one or more data centers. Local Internet Protocol (IP) addresses 916 may be associated with the resource instances 912; the local IP addresses are the internal network addresses of the resource instances 912 on the provider network 900. In some embodiments, the provider network 900 may also provide public IP addresses 914 and/or public IP address ranges (e.g., Internet Protocol version 4 (IPv4) or Internet Protocol version 6 (IPv6) addresses) that customers may obtain from the provider 900.

Conventionally, the provider network 900, via the virtualization services 910, may allow a customer of the service provider (e.g., a customer that operates one or more client networks 950A-950C including one or more customer device(s) 952) to dynamically associate at least some public IP addresses 914 assigned or allocated to the customer with particular resource instances 912 assigned to the customer. The provider network 900 may also allow the customer to remap a public IP address 914, previously mapped to one virtualized computing resource instance 912 allocated to the customer, to another virtualized computing resource instance 912 that is also allocated to the customer. Using the virtualized computing resource instances 912 and public IP addresses 914 provided by the service provider, a customer of the service provider such as the operator of customer network(s) 950A-950C may, for example, implement customer-specific applications and present the customer's applications on an intermediate network 940, such as the Internet. Other network entities 920 on the intermediate network 940 may then generate traffic to a destination public IP address 914 published by the customer network(s) 950A-950C; the traffic is routed to the service provider data center, and at the data center is routed, via a network substrate, to the local IP address 916 of the virtualized computing resource instance 912 currently mapped to the destination public IP address 914. Similarly, response traffic from the virtualized computing resource instance 912 may be routed via the network substrate back onto the intermediate network 940 to the source entity 920.

Local IP addresses, as used herein, refer to the internal or "private" network addresses, for example, of resource instances in a provider network. Local IP addresses can be within address blocks reserved by Internet Engineering Task Force (IETF) Request for Comments (RFC) 1918 and/or of an address format specified by IETF RFC 4193 and may be mutable within the provider network. Network traffic originating outside the provider network is not directly routed to local IP addresses; instead, the traffic uses public IP addresses that are mapped to the local IP addresses of the resource instances. The provider network may include networking devices or appliances that provide network address translation (NAT) or similar functionality to perform the mapping from public IP addresses to local IP addresses and vice versa.

Public IP addresses are Internet mutable network addresses that are assigned to resource instances, either by the service provider or by the customer. Traffic routed to a public IP address is translated, for example via 1:1 NAT, and forwarded to the respective local IP address of a resource instance.

Some public IP addresses may be assigned by the provider network infrastructure to particular resource instances; these public IP addresses may be referred to as standard public IP addresses, or simply standard IP addresses. In some embodiments, the mapping of a standard IP address to a local IP address of a resource instance is the default launch configuration for all resource instance types.

At least some public IP addresses may be allocated to or obtained by customers of the provider network 900; a customer may then assign their allocated public IP addresses to particular resource instances allocated to the customer. These public IP addresses may be referred to as customer public IP addresses, or simply customer IP addresses. Instead of being assigned by the provider network 900 to resource instances as in the case of standard IP addresses, customer IP addresses may be assigned to resource instances by the customers, for example via an API provided by the service provider. Unlike standard IP addresses, customer IP addresses are allocated to customer accounts and can be remapped to other resource instances by the respective customers as necessary or desired. A customer IP address is associated with a customer's account, not a particular resource instance, and the customer controls that IP address until the customer chooses to release it. Unlike conventional static IP addresses, customer IP addresses allow the customer to mask resource instance or availability zone failures by remapping the customer's public IP addresses to any resource instance associated with the customer's account. The customer IP addresses, for example, enable a customer to engineer around problems with the customer's resource instances or software by remapping customer IP addresses to replacement resource instances.

Figure 10:
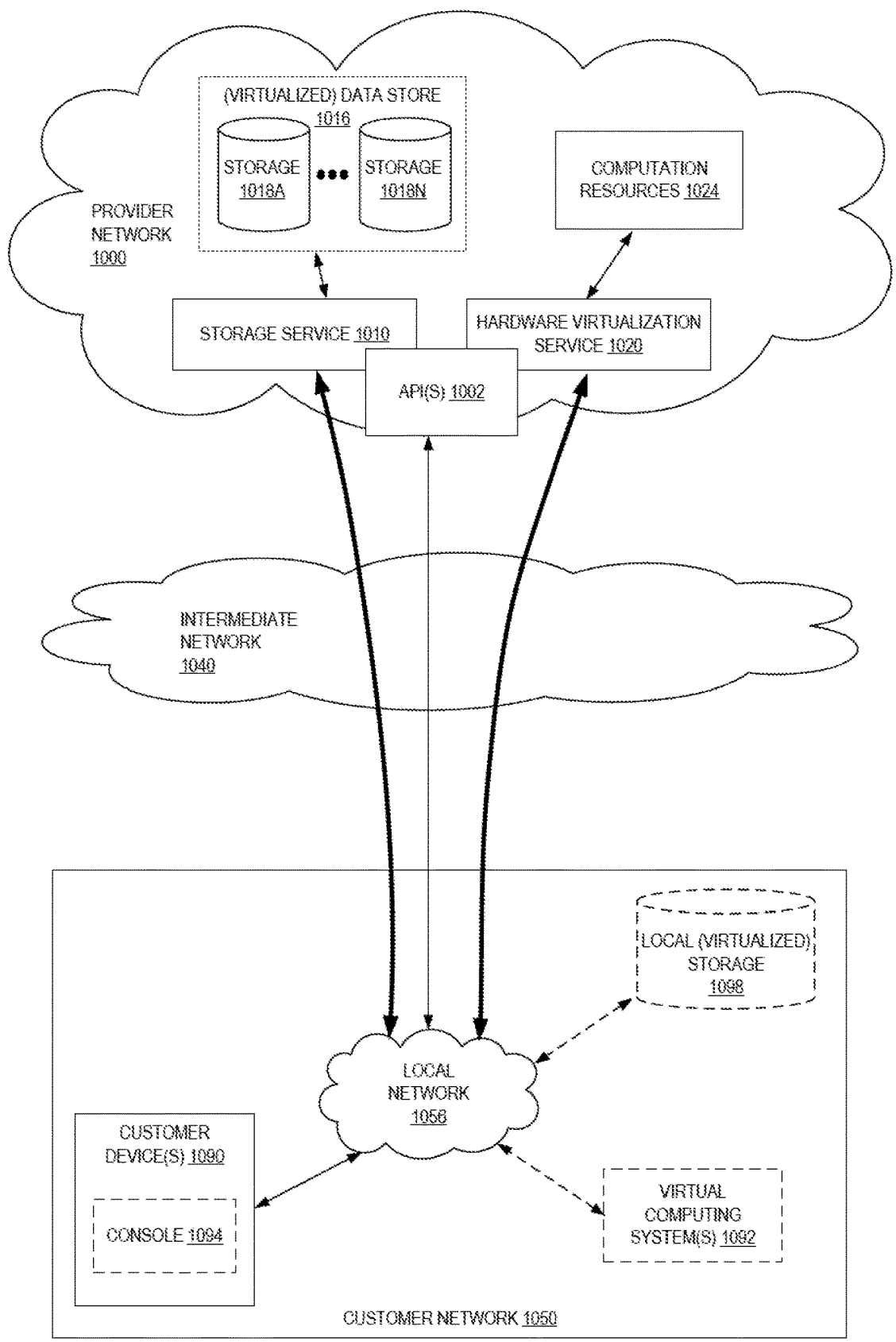
FIG. 10 is a block diagram of an example provider network that provides a storage service and a hardware virtualization service to customers according to some embodiments.

FIG. 10 is a block diagram of an example provider network that provides a storage service and a hardware virtualization service to customers, according to some embodiments. Hardware virtualization service 1020 provides multiple computation resources 1024 (e.g., VMs) to customers. The computation resources 1024 may, for example, be rented or leased to customers of the provider network 1000 (e.g., to a customer that implements customer network 1050). Each computation resource 1024 may be provided with one or more local IP addresses. Provider network 1000 may be configured to route packets from the local IP addresses of the computation resources 1024 to public Internet destinations, and from public Internet sources to the local IP addresses of computation resources 1024.

Provider network 1000 may provide a customer network 1050, for example coupled to intermediate network 1040 via local network 1056, the ability to implement virtual computing systems 1092 via hardware virtualization service 1020 coupled to intermediate network 1040 and to provider network 1000. In some embodiments, hardware virtualization service 1020 may provide one or more APIs 1002, for example a web services interface, via which a customer network 1050 may access functionality provided by the hardware virtualization service 1020, for example via a console 1094 (e.g., a web-based application, standalone application, mobile application, etc.). In some embodiments, at the provider network 1000, each virtual computing system 1092 at customer network 1050 may correspond to a computation resource 1024 that is leased, rented, or otherwise provided to customer network 1050.

From an instance of a virtual computing system 1092 and/or another customer device 1090 (e.g., via console 1094), the customer may access the functionality of storage service 1010, for example via one or more APIs 1002, to access data from and store data to storage resources 1018A-1018N of a virtual data store 1016 (e.g., a folder or "bucket", a virtualized volume, a database, etc.) provided by the provider network 1000. In some embodiments, a virtualized data store gateway (not shown) may be provided at the customer network 1050 that may locally cache at least some data, for example frequently-accessed or critical data, and that may communicate with storage service 1010 via one or more communications channels to upload new or modified data from a local cache so that the primary store of data (virtualized data store 1016) is maintained. In some embodiments, a user, via a virtual computing system 1092 and/or on another customer device 1090, may mount and access virtual data store 1016 volumes via storage service 1010 acting as a storage virtualization service, and these volumes may appear to the user as local (virtualized) storage 1098.

While not shown in FIG. 10, the virtualization service(s) may also be accessed from resource instances within the provider network 1000 via API(s) 1002. For example, a customer, appliance service provider, or other entity may access a virtualization service from within a respective virtual network on the provider network 1000 via an API 1002 to request allocation of one or more resource instances within the virtual network or within another virtual network.

Illustrative Systems

Figure 11:
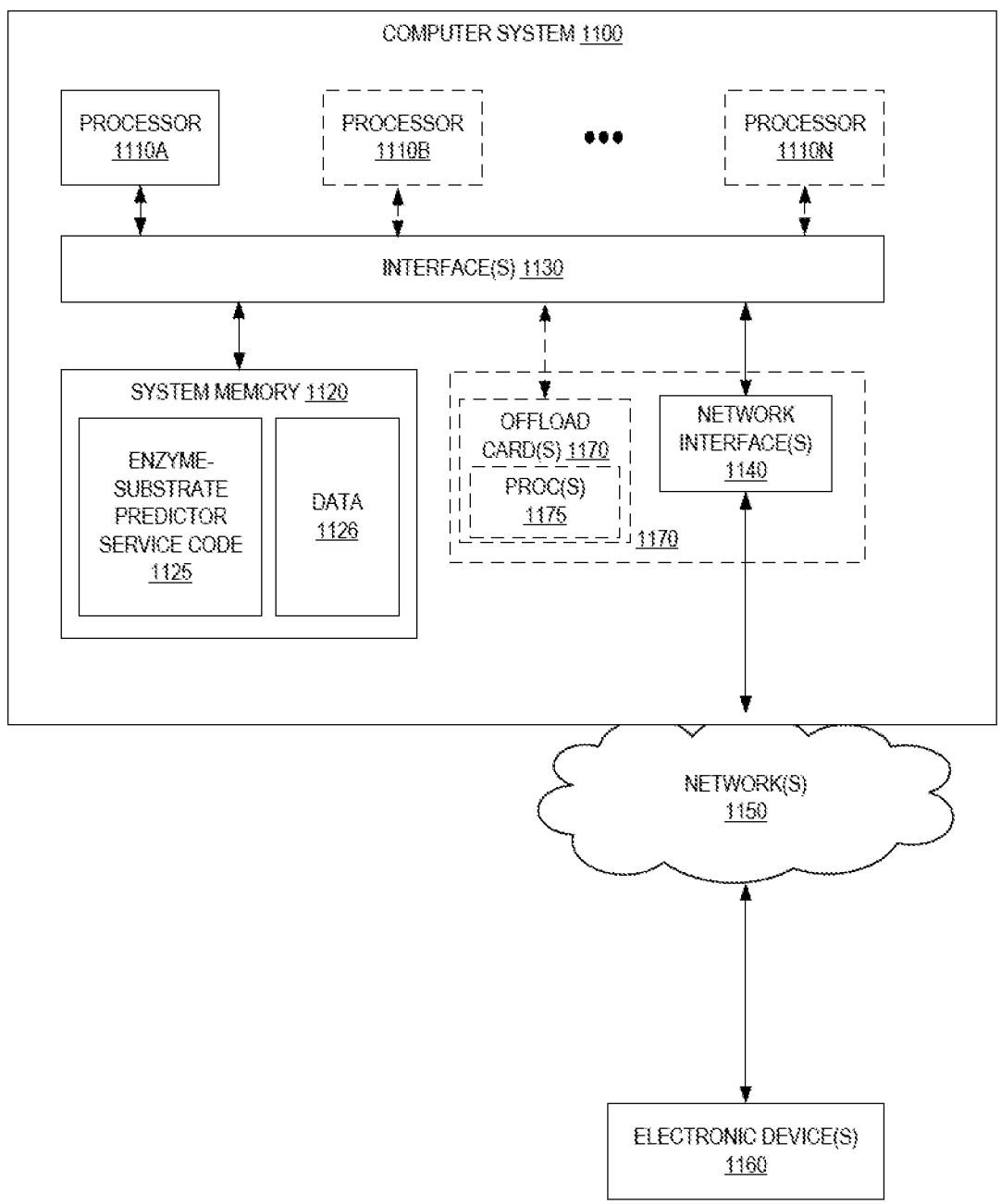
FIG. 11 is a block diagram illustrating an example computer system that may be used in some embodiments.

In some embodiments, a system that implements a portion or all of the techniques described herein may include a general-purpose computer system that includes or is configured to access one or more computer-accessible media, such as computer system 1100 illustrated in FIG. 11. In the illustrated embodiment, computer system 1100 includes one or more processors 1110 coupled to a system memory 1120 via an input/output (I/O) interface 1130. Computer system 1100 further includes a network interface 1140 coupled to I/O interface 1130. While FIG. 11 shows computer system 1100 as a single computing device, in various embodiments a computer system 1100 may include one computing device or any number of computing devices configured to work together as a single computer system 1100.

In various embodiments, computer system 1100 may be a uniprocessor system including one processor 1110, or a multiprocessor system including several processors 1110 (e.g., two, four, eight, or another suitable number). Processors 1110 may be any suitable processors capable of executing instructions. For example, in various embodiments, processors 1110 may be general-purpose or embedded processors implementing any of a variety of instruction set architectures (ISAs), such as the x86, ARM, PowerPC, SPARC, or MIPS ISAs, or any other suitable ISA. In multiprocessor systems, each of processors 1110 may commonly, but not necessarily, implement the same ISA.

System memory 1120 may store instructions and data accessible by processor(s) 1110. In various embodiments, system memory 1120 may be implemented using any suitable memory technology, such as random-access memory (RAM), static RAM (SRAM), synchronous dynamic RAM (SDRAM), nonvolatile/Flash-type memory, or any other type of memory. In the illustrated embodiment, program instructions and data implementing one or more desired functions, such as those methods, techniques, and data described above are shown stored within system memory 1120 as enzyme-substrate predictor service code 1125 and data 1126.

In one embodiment, I/O interface 1130 may be configured to coordinate I/O traffic between processor 1110, system memory 1120, and any peripheral devices in the device, including network interface 1140 or other peripheral interfaces. In some embodiments, I/O interface 1130 may perform any necessary protocol, timing or other data transformations to convert data signals from one component (e.g., system memory 1120) into a format suitable for use by another component (e.g., processor 1110). In some embodiments, I/O interface 1130 may include support for devices attached through various types of peripheral buses, such as a variant of the Peripheral Component Interconnect (PCI) bus standard or the Universal Serial Bus (USB) standard, for example. In some embodiments, the function of I/O interface 1130 may be split into two or more separate components, such as a north bridge and a south bridge, for example. Also, in some embodiments some or all of the functionality of I/O interface 1130, such as an interface to system memory 1120, may be incorporated directly into processor 1110.

Network interface 1140 may be configured to allow data to be exchanged between computer system 1100 and other devices 1160 attached to a network or networks 1150, such as other computer systems or devices as illustrated in FIG. 1, for example. In various embodiments, network interface 1140 may support communication via any suitable wired or wireless general data networks, such as types of Ethernet network, for example. Additionally, network interface 1140 may support communication via telecommunications/telephony networks such as analog voice networks or digital fiber communications networks, via storage area networks (SANs) such as Fibre Channel SANs, or via I/O any other suitable type of network and/or protocol.

In some embodiments, a computer system 1100 includes one or more offload cards 1170 (including one or more processors 1175, and possibly including the one or more network interfaces 1140) that are connected using an I/O interface 1130 (e.g., a bus implementing a version of the Peripheral Component Interconnect Express (PCI-E) standard, or another interconnect such as a QuickPath interconnect (QPI) or UltraPath interconnect (UPI)). For example, in some embodiments the computer system 1100 may act as a host electronic device (e.g., operating as part of a hardware virtualization service) that hosts compute instances, and the one or more offload cards 1170 execute a virtualization manager that can manage compute instances that execute on the host electronic device. As an example, in some embodiments the offload card(s) 1170 can perform compute instance management operations such as pausing and/or un-pausing compute instances, launching and/or terminating compute instances, performing memory transfer/copying operations, etc. These management operations may, in some embodiments, be performed by the offload card(s) 1170 in coordination with a hypervisor (e.g., upon a request from a hypervisor) that is executed by the other processors 1110A-1110N of the computer system 1100. However, in some embodiments the virtualization manager implemented by the offload card(s) 1170 can accommodate requests from other entities (e.g., from compute instances themselves), and may not coordinate with (or service) any separate hypervisor.

In some embodiments, system memory 1120 may be one embodiment of a computer-accessible medium configured to store program instructions and data as described above. However, in other embodiments, program instructions and/or data may be received, sent, or stored upon different types of computer-accessible media. Generally speaking, a computer-accessible medium may include non-transitory storage media or memory media such as magnetic or optical media, e.g., disk or DVD/CD coupled to computer system 1100 via I/O interface 1130. A non-transitory computer-accessible storage medium may also include any volatile or non-volatile media such as RAM (e.g., SDRAM, double data rate (DDR) SDRAM, SRAM, etc.), read only memory (ROM), etc., that may be included in some embodiments of computer system 1100 as system memory 1120 or another type of memory. Further, a computer-accessible medium may include transmission media or signals such as electrical, electromagnetic, or digital signals, conveyed via a communication medium such as a network and/or a wireless link, such as may be implemented via network interface 1140.

Various embodiments discussed or suggested herein can be implemented in a wide variety of operating environments, which in some cases can include one or more user computers, computing devices, or processing devices which can be used to operate any of a number of applications. User or client devices can include any of a number of general-purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems, and/or other devices capable of communicating via a network.

Most embodiments utilize at least one network that would be familiar to those skilled in the art for supporting communications using any of a variety of widely-available protocols, such as Transmission Control Protocol/Internet Protocol (TCP/IP), File Transfer Protocol (FTP), Universal Plug and Play (UPnP), Network File System (NFS), Common Internet File System (CIFS), Extensible Messaging and Presence Protocol (XMPP), AppleTalk, etc. The network(s) can include, for example, a local area network (LAN), a wide-area network (WAN), a virtual private network (VPN), the Internet, an intranet, an extranet, a public switched telephone network (PSTN), an infrared network, a wireless network, and any combination thereof.

In embodiments utilizing a web server, the web server can run any of a variety of server or mid-tier applications, including HTTP servers, File Transfer Protocol (FTP) servers, Common Gateway Interface (CGI) servers, data servers, Java servers, business application servers, etc. The server(s) also may be capable of executing programs or scripts in response requests from user devices, such as by executing one or more Web applications that may be implemented as one or more scripts or programs written in any programming language, such as Java®, C, C # or C++, or any scripting language, such as Perl, Python, PHP, or TCL, as well as combinations thereof. The server(s) may also include database servers, including without limitation those commercially available from Oracle®, Microsoft®, Sybase®, IBM®, etc. The database servers may be relational or non-relational (e.g., "NoSQL"), distributed or non-distributed, etc.

Environments disclosed herein can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and/or at least one output device (e.g., a display device, printer, or speaker). Such a system may also include one or more storage devices, such as disk drives, optical storage devices, and solid-state storage devices such as random-access memory (RAM) or read-only memory (ROM), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory (EEPROM), flash memory or other memory technology, Compact Disc-Read Only Memory (CD-ROM), Digital Versatile Disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

In the preceding description, various embodiments are described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Bracketed text and blocks with dashed borders (e.g., large dashes, small dashes, dot-dash, and dots) are used herein to illustrate optional operations that add additional features to some embodiments. However, such notation should not be taken to mean that these are the only options or optional operations, and/or that blocks with solid borders are not optional in certain embodiments.

Reference numerals with suffix letters may be used to indicate that there can be one or multiple instances of the referenced entity in various embodiments, and when there are multiple instances, each does not need to be identical but may instead share some general traits or act in common ways. Further, the particular suffixes used are not meant to imply that a particular amount of the entity exists unless specifically indicated to the contrary. Thus, two entities using the same or different suffix letters may or may not have the same number of instances in various embodiments.

References to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Moreover, in the various embodiments described above, unless specifically noted otherwise, disjunctive language such as the phrase "at least one of A, B, or C" is intended to be understood to mean either A, B, or C, or any combination thereof (e.g., A, B, and/or C). As such, disjunctive language is not intended to, nor should it be understood to, imply that a given embodiment requires at least one of A, at least one of B, or at least one of C to each be present.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

What is claimed is:

1. A computer-implemented method comprising:
receiving, by one or more processors of a computing device, a request to predict a pair of an enzyme primary sequence and a substrate, and an interaction probability for the pair, the request including a representation of a primary sequence of an enzyme, a representation of a substrate composition, and an indication of reactivity of the substrate and the enzyme;
applying, by the one or more processors, an embedding to the representation of the primary sequence of the enzyme to generate an enzyme vector;
decomposing, by the one or more processors, the substrate into a 2-D connection matrix with 1-D embeddings for each node of the 2-D connection matrix;
tiling, by the one or more processors, the 1-D embeddings to form 2-D representations for each node of the 2-D connection matrix;
stacking, by the one or more processors, the 2-D connection matrix with the 2-D representations and upsampling, thereby generating a 2-D upsampled stack;
convolving, by the one or more processors, the 2-D upsampled stack to generate a substrate vector;
concatenating, by the one or more processors, the enzyme vector, substrate vector, and interaction indication to form a machine learning (ML) model input;
receiving, by a multi-headed self-attention ML model executed by the one or more processors, the ML input;
predicting, using the multi-headed self-attention ML model based at least on the ML input, one or more pairs of an enzyme primary sequence and a substrate, and an interaction probability for each pair; and
outputting, by the multi-headed self-attention ML model, a result of the predicting using the multi-headed self-attention ML model, the result including the one or more pairs of an enzyme primary sequence and a substrate, and an interaction probability for each pair.

2. The computer-implemented method of claim 1, wherein the representation of the primary sequence of the enzyme utilizes an amino acid code consistent with International Union of Pure and Applied Chemistry usage.

3. The computer-implemented method of claim 1, wherein the multi-headed self-attention ML model is a transformer-based model.

4. A computer-implemented method comprising:
receiving, by one or more processors of a computing device, a request to predict a pair of an enzyme primary sequence and a substrate, and an interaction probability for the pair;
generating a substrate vector by:
decomposing the substrate into a 2-D connection matrix with 1-D embeddings for each node of the 2-D connection matrix;
tiling the 1-D embeddings to form 2-D representations for each node of the 2-D connection matrix;
stacking the 2-D connection matrix with the 2-D representations and upsampling, thereby generating a 2-D upsampled stack; and
convolving the 2-D upsampled stack to generate the substrate vector;
combining, by the one or more processors, an enzyme vector, the substrate vector, and an interaction indication for the enzyme and substrate to form a machine learning (ML) model input;
receiving, by a multi-headed self-attention ML model executed by the one or more processors, the ML model input;
predicting, using the multi-headed self-attention ML model based at least on the ML model input, the pair of an enzyme primary sequence and a substrate, and an interaction probability for the pair; and
outputting, by the multi-headed self-attention ML model, a result of the predicting using the multi-headed self-attention ML model, the result including the pair of an enzyme primary sequence and a substrate, and an interaction probability for the pair.

5. The computer-implemented method of claim 4, wherein the enzyme vector is generated by applying an embedding to a representation of a primary sequence of an enzyme.

6. The computer-implemented method of claim 5, wherein the representation of the primary sequence of the enzyme is a character-based representation.

7. The computer-implemented method of claim 6, wherein characters of the character-based representation conform to an amino acid code consistent with International Union of Pure and Applied Chemistry usage.

8. The computer-implemented method of claim 4, wherein the enzyme vector, the substrate vector, and the interaction indication are included in the request.

9. The computer-implemented method of claim 4, wherein the multi-headed self-attention ML model is a transformer-based model.

10. The computer-implemented method of claim 4, wherein combining the enzyme vector, the substrate vector, and the interaction indication for the enzyme and substrate to form the ML model input comprises concatenating the enzyme vector, the substrate vector, and the interaction indication for the enzyme and substrate.

11. The computer-implemented method of claim 4, wherein the interaction indication for the enzyme and substrate is binary.

12. The computer-implemented method of claim 4, further comprising generating a 3-D representation from the result of the predicting using the multi-headed self-attention ML model.

13. A system comprising:
a first one or more electronic devices including one or more processors and memory storing instructions that upon execution by the one or more processors cause the first one or more electronic devices to:
receive a request to predict a pair of an enzyme primary sequence and a substrate, and an interaction probability for the pair;
generate a substrate vector by:
decomposing the substrate into a 2-D connection matrix with 1-D embeddings for each node of the 2-D connection matrix;
tiling the 1-D embeddings to form 2-D representations for each node of the 2-D connection matrix;
stacking the 2-D connection matrix with the 2-D representations and upsampling, thereby generating a 2-D upsampled stack; and
convolving the 2-D upsampled stack to generate the substrate vector;

combine an enzyme vector, the substrate vector, and an interaction indication for the enzyme and substrate to form a machine learning (ML) model input;

receive, by a multi-headed self-attention ML model executed by the one or more processors, the ML model input;

predict, using the multi-headed self-attention ML model based at least on the ML model input, the pair of an enzyme primary sequence and a substrate, and an interaction probability for the pair; and output, by the multi-headed self-attention ML model, a result of the predicting using the multi-headed self-attention ML model, the result including the pair of an enzyme primary sequence and a substrate, and an interaction probability for the pair; and a second one or more electronic devices including one or more processors and memory storing instructions that upon execution by the one or more processors cause the second one or more electronic devices to generate a 3-D representation of an enzyme based on the result.

14. The system of claim 13, wherein the enzyme vector is generated by applying an embedding to a representation of a primary sequence of an enzyme.

15. The system of claim 14, wherein the representation of the primary sequence of the enzyme is a character-based representation.

16. The system of claim 15, wherein characters of the character-based representation conform to an amino acid code consistent with International Union of Pure and Applied Chemistry usage.

17. The system of claim 13, wherein the multi-headed self-attention ML model is a transformer-based model.

18. The system of claim 13, wherein the interaction indication for the enzyme and substrate is binary.

19. The system of claim 13, wherein the enzyme vector, the substrate vector, and the interaction indication are included in the request.

20. The system of claim 13, wherein combining the enzyme vector, the substrate vector, and the interaction indication for the enzyme and substrate to form the ML model input comprises concatenating the enzyme vector, the substrate vector, and the interaction indication for the enzyme and substrate.

* * * * *